United States Patent [19]
Freese et al.

[11] Patent Number: 5,533,998
[45] Date of Patent: Jul. 9, 1996

[54] APPARATUS AND METHOD FOR LASER CYCLO-PHOTOCOAGULATION

[75] Inventors: Manfred Freese, Richmond Hill, Canada; Peter Reimer, Ellwangen; Theo Lasser, Oberkochen, both of Germany

[73] Assignee: Carl-Zeiss-Stiftung, Heidenheim, Germany

[21] Appl. No.: 354,404

[22] Filed: Dec. 12, 1994

[30] Foreign Application Priority Data

Dec. 21, 1993 [DE] Germany ............... 43 43 699.4
Aug. 30, 1994 [DE] Germany ............... 44 30 720.9

[51] Int. Cl.$^6$ ..................................... A61N 5/06
[52] U.S. Cl. ........................................... 606/4
[58] Field of Search ............... 606/4, 5, 6, 10, 606/11, 12, 14, 15, 16, 17; 128/660.06, 660.09; 607/97

[56] References Cited

U.S. PATENT DOCUMENTS

| | | | |
|---|---|---|---|
| 5,285,788 | 2/1994 | Arenson et al. | 128/660.06 |
| 5,293,871 | 3/1994 | Reinstein et al. | 128/660.06 |
| 5,369,454 | 11/1994 | Reinstein et al. | 351/201 |

FOREIGN PATENT DOCUMENTS 9216259  10/1992  WIPO ........................ A16N 5/06

OTHER PUBLICATIONS

"Ultraschall inder opthalmologischen Dignostik", Von Rudolf Guthoff.
"Medical Imaging Systems for Feedback Control of Interstitial Laser Photocoagulation", Douglas R. Wyman et al, IEEE vol. 80 No. 6 Jun. 1992.
"Surface Ultrasound Microscopic Imaging of the Intact Eye", Charles Pavlin et al Opthalmology 1990:97:244–250.
"Clinical Use of Ultrasound Biomicroscopy" Charles Pavlin et al, Opthalmology 1991; 98:287–295.

*Primary Examiner*—Angela D. Sykes
*Assistant Examiner*—Sonya Harris-Ogugua

[57] ABSTRACT

A laser cyclo-photocoagulation in the eye is monitored on-line by means of an ultrasonic biomicroscope, i.e., visual representations of the treated field, inclusive of the effects obtained in the tissue, are provided continuously on a display placed at the disposal of the attending doctor. The doctor decides, by means of the generated ultrasonic images, on the course of the further treatment. The choice is possible between different operating modes of the ultrasonic biomicroscope.

16 Claims, 5 Drawing Sheets

APPARATUS AND METHOD FOR LASER CYCLO-PHOTOCOAGULATION

BACKGROUND OF THE INVENTION

1. Field of the Invention

The present invention relates to an apparatus and a method for laser cyclophotocoagulation.

Very varied pharmacological and surgical methods have been proposed for the treatment of glaucoma, i.e., for the reduction of pathologically increased internal ocular pressure. A relatively new surgical method for the improvement of the uveoscleral chamber water drainage is represented by so-called laser cyclophotocoagulation. A description of this method was, for example, given by D. E. Gaasterland et al. The abstract of his lectures can be found in Invest. Ophthalmol. and Visual Sci., Vol. 33, 1992, pp. 1644, entitled "A Multicenter Study of Contact Diode Laser Transscleral Cyclophoto-Coagulation in Glaucoma Patients".

In this method, laser coagulation centers are set up in the sclera of the eye by means of a fiber applicator of spiral or circular shape. A direct destruction of the ciliary epithelium which produces ciliary water results in the induced zones of necrosis, with the consequence of a reduced chamber water production and the lowering of the internal ocular pressure.

2. Relevant Prior Art

Suitable fiber applicators for such a method have to some extent been described in the international patent application WO 92/16259.

However, it has long been considered the most aggravating disadvantage of this method that no kind of feedback is available to the attending doctor concerning the coagulation centers which are set up or the resulting effects in the zones of necrosis. Thus some degree of uncertainty arises as to the extent to which the number of the coagulation centers set up, and/or the applied laser power, is sufficient or possibly has to be changed in the course of further treatment.

SUMMARY OF THE INVENTION

The object of the present invention is hence to provide an apparatus and also a method for laser cyclophotocoagulation, by means of which reliable information concerning the effects arising are placed, on line as far as possible, at the disposal of the attending doctor. The aim is to achieve a more targeted dosing of the applied laser radiation than has heretofore been possible, in order thus to minimize the risk in such a treatment.

According to the invention, laser cyclophotocoagulation is now supplemented by simultaneous on line monitoring by means of an ultrasonic biomicroscope, so that it is ensured, by means of a defined relative orientation between the ultrasonic head of an ultrasonic biomicroscope and the fiber applicator used, that visualization is always possible of the region which has actually just been treated. In particular, a defined relative arrangement of this kind offers a series of advantages in comparison with the heretofore proposed combinations of ultrasonically supported image processing and laser surgery. In this connection, the publication of F. R. Wyman et al., "Medical Imaging Systems for Feedback Control of Interstitial Laser Photocoagulation" in Proceedings of IEEE, Vol. 80, No. 6, pp. 890–902, may be referred to.

The attending doctor now receives current information concerning the present course of treatment, presented on a suitable display. It is thus possible to decide, based on the information supplied by the ultrasonic biomicroscope, whether the course of the coagulation has so far had correct results, or the dosage of laser power has to be different, or else how the treatment has to proceed, at any given time, in another manner.

The ultrasonic microscope used can here be used in various modes of operation, i.e., in particular either in the so-called A-image technique or the B-image technique. The doctor has the possibility of selecting during the course of the treatment, according to requirements, alternatively between these two modes of operation.

A particularly advantageous method in the form of the suitable combination of these two modes of operation is the subject of the invention. While the site of treatment is localized as exactly as possible by means of the mode of operation of the B-image technique, the on line monitoring and control of the coagulation centers which are set up takes place in the subsequent course of the cyclophotocoagulation proper by the operating mode of the A-image technique.

The possible visual representation of the treated region in the eye in the B-image technique then simultaneously shows the distal end of the fiber applicator and also the coagulation center set up in the eye, in a sectional image. The sectional images are then advantageously prepared, e.g., on a suitable false color representation on the display, such that as reliable as possible an interpretation by the attending doctor is possible.

On the other hand, with the selection of the A-image technique, a graphical representation in the form of a one-dimensional depth image with the reflecting boundary surfaces in the ocular region of interest is presented to the doctor.

Alternatively, however, it is also possible, particularly with the A-image technique, to evaluate in an automated manner the information supplied concerning the coagulation centers set up, and to generate suitable signals which are further used, via a control or regulating circuit, for the regulation of the laser used. The treatment site, or respectively the coagulation center, is localized as precisely as possible by means of the B-image technique before such an automated evaluation by the A-image technique.

A low-risk and more closely targeted dosing of the applied laser radiation results at any given time, both in the evaluation of the image information by the doctor and also in the automated evaluation by means of a control circuit.

A suitable apparatus for carrying out the method according to the invention advantageously provides a fixing apparatus filled with a suitable liquid, with the ultrasonic head of the ultrasonic biomicroscope dipping into this liquid. The fixing apparatus used serves both to stabilize the patient's eye in the course of the treatment and also to keep the liquid in place on the patient's eye.

In a possible embodiment of the fixing apparatus, on the contrary, a defined spatial coupling between the distal end of the laser applicator and the ultrasonic head is constantly provided, so that the scan plane monitored in, e.g., the B-image technique is oriented in a defined relative position to the fiber applicator and to the place of treatment.

In an alternative further embodiment of such a fixing apparatus, the distal end of a fiber applicator and also the eye to be treated are arranged in a defined and reproducible relative relationship to each other.

The ultrasonic biomicroscope has a following evaluation unit and image processing unit, including a display on which the information about the region of the eye which is concerned can be represented according to the selected mode of operation.

BRIEF DESCRIPTION OF THE DRAWINGS

Further advantages and also details of the apparatus according to the invention and of the method according to the invention will become apparent from the following description of embodiment examples with reference to the accompanying drawings, in which:

FIG. 2b shows a perspective representation of the embodiment example of a fixing apparatus shown in FIG. 2a;

DETAILED DESCRIPTION OF PREFERRED EMBODIMENTS

Figure 1:
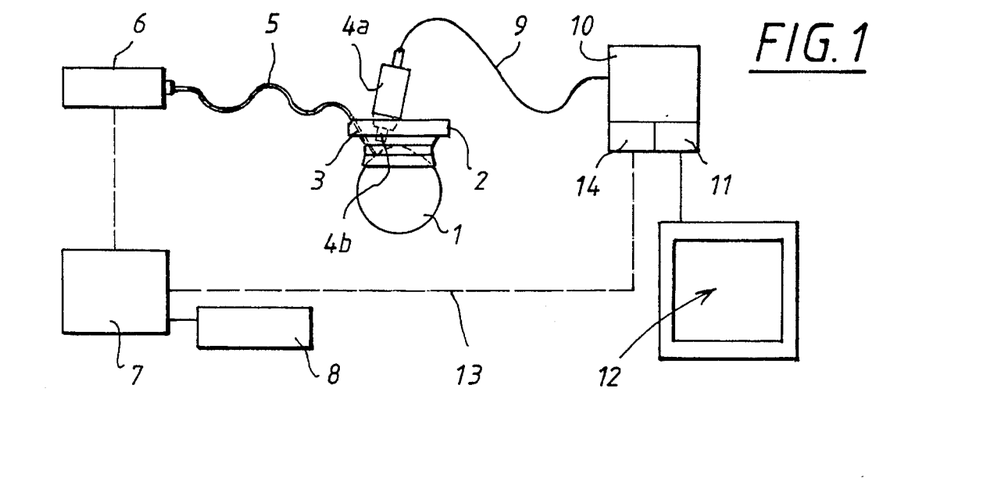
FIG. 1 shows the apparatus according to the invention including important components, in a schematized representation.

In FIG. 1, the apparatus according to the invention, including the most important necessary components, is shown schematically in the form of a block circuit diagram.

A fixing apparatus (2) is arranged on the eye (1) to be treated, and on the one hand serves to fix the eye in a defined or reproducible position during the operation.

Moreover a liquid is kept in place by means of the fixing apparatus (2) and produces the acoustic coupling between the ultrasonic head (4b) of the ultrasonic biomicroscope and the eye (1); water or a suitable gel can be used for this purpose. A liquid which has only a small difference in impedance from the directly adjacent tissues of the eye, so that the boundary surface between the liquid and the eye provides no excessively intense ultrasonic signal which would mask the proper signals of interest derived from the deeper-lying regions of the eye, has been found to be particularly advantageous here.

As an alternative to the embodiment shown in FIG. 1, the required acoustic coupling can also be produced by direct contact or by the use of a closed preliminary water path between the ultrasonic head and the cornea of the eye.

Two different embodiments of a suitable fixing apparatus are described in further detail below, with reference to FIGS. 2a, 2b, 2c and 3.

The ultrasonic head (4b) of the ultrasonic biomicroscope is arranged in a suitable housing (4a), the defined mobility of the ultrasonic head (4b) in the housing (4a) being ensured, in order in particular to make possible the scanning, which is necessary for the production of the B-image, of the ultrasonic head (4b) in a defined plane.

The ultrasonic head (4b) is arranged, according to the invention, in a defined relative position to the distal end of the fiber applicator (3) and to the region to be treated in the eye (1). Advantageously, the alignment of the ultrasonic head (4b), as shown in FIG. 1, takes place such that, in particular in the operating mode of the B-image technique, the distal end of the fiber applicator (3) and also the coagulation center in the eye can be visualized on the display. For this purpose, the ultrasonic head (4b) in the embodiment example shown is aligned such that a scanning of the ultrasonic head (4b) is possible in a plane which corresponds to the plane of the drawing.

The fiber applicator (3) used is fed via a fiber optic light guide (5) by a laser (6), the exit radiation of which is coupled into the fiber optic light guide (5). Suitable lasers may be a diode laser or a solid state laser, e.g., a Nd:YAG laser, which preferably emit in the wavelength region between 0.5 μm and 1.7 μm. These wavelengths effect the desired coagulatory effect in the ciliary body of the patient's eye, i.e. lastly the desired reduction of the chamber water production.

A suitable laser power is in the region of 0.5 W–3 W.

Different laser parameters, such as the delivered power or the time of action on the eye, are varied by means of a central control unit (7). The control unit (7) preferably includes for this purpose an input interface (8) for the attending doctor, by means of which both the laser parameters mentioned above and also different further ones can be manually varied and set.

The ultrasonic head (4b) of the ultrasonic biomicroscope is connected by a suitable signal conductor (9) to a signal processing unit (10) which, in a known manner in an image processing stage (11), converts the registered signals into image information on a display (12).

As has already been mentioned several times, the signal processing unit (10) is capable of effecting different operating modes of the ultrasonic biomicroscope. Of particular advantage here is at least one possibility of choice between the A- and B-image technique and the corresponding representation on the display.

Reference may be made, regarding these ultrasonic evaluation techniques, to the monograph, "Ultrasonics in Ophthalmological Diagnosis" by R. Guthoff (F. Enke Verlag, Stuttgart, 1988) where these evaluation techniques are presented, e.g., in Chapter 1.

Moreover, reference may be made as regards the mode of functioning of a suitable ultrasonic biomicroscope, including the image processing thereby possible, to the publications, J. Pavlin et al., "Clinical Use of Ultrasound Biomicroscopy" in Ophthalmology 98, pp. 287–295, 1991 and to J. Pavlin et al., "Subsurface Ultrasound Microscopic Imaging of the Intact Eye" in Ophthalmology 97, pp. 244–250, 1990.

While, by means of the B-image technique, both the fiber applicator and the treatment site in the tissue can be visualized two-dimensionally in a sectional image on the display, the A-image technique makes possible a graphical representation of distances of reflecting boundary surfaces in a chosen direction. The corresponding graphical representations on the display (12) are explained below in further detail with reference to FIGS. 4a–b and 5a–c.

The ultrasonic microscope used operates in a frequency region which is suited to the tissue to be observed or to the specific ultrasonic characteristics. Suitable sonic frequencies then lie in the region of 25–75 Mhz, where 50 MHz has been found to be particularly advantageous as regards the required resolving power.

It is now possible, according to the invention, for the attending doctor to himself evaluate the image information shown on the display (12) and to vary the laser parameters corresponding to the observed effects in the eye (1). Thus the doctor can decide, when the desired coagulation effects so far obtained in the eye are not yet sufficiently pronounced, to increase the laser power or else to extend the treatment time, and so on.

As an alternative to evaluating the visual information on the display, a control or regulating circuit can however also be embodied in the form of a direct signal connection (13) between the control unit (7) of the laser (6) and the signal processing unit (10) of the ultrasonic microscope. An evaluation stage (14), which converts ultrasonic signals registered by the ultrasonic head (4b) into corresponding control signals for the control unit (7) of the laser (6), is required for this purpose in the signal processing unit (10) of the ultrasonic microscope. For this, the desired treatment site is first localized in the B-image technique, and then the signals provided by the A-image technique are evaluated in the region of the treatment site.

The evaluation of the information supplied from this region can take place, e.g., in a manner such that, for a registered ultrasonic signal from this region, a corresponding laser parameter combination is passed to the control unit (7), by the use of stored reference tables, etc.

The attending doctor advantageously has the possibility of choosing between the two kinds of operation which have been described, with direct evaluation of the ultrasonic signals by means of the control or regulating circuit, or with indirect visual evaluation by means of the observed images on the display. For this purpose, the apparatus according to the invention has a suitable capability of changing over.

There now results overall a more reliable treatment with immediate feedback between therapy and diagnosis. Because of the on-line monitoring, peculiarities which are specific to the patient can then also be taken into account.

A first embodiment example of a suitable fixing apparatus (2) within the apparatus according to the invention will be described below with reference to FIGS. 2a–2c. Insofar as the same components are shown as in FIG. 1, the same reference numerals are also used for these components.

Figure 2A:
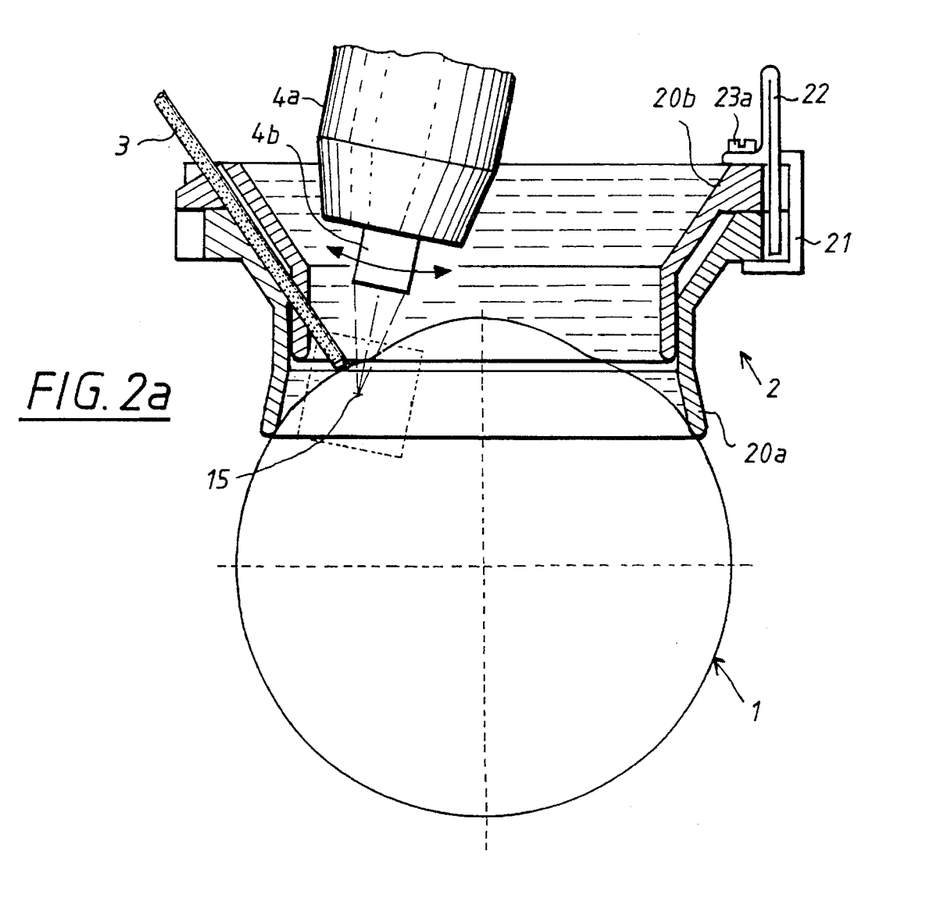
FIG. 2a shows a first embodiment example of a fixing apparatus set on the patient's eye with the ultrasonic head of the ultrasonic biomicroscope and the fiber applicator in a side view.

FIG. 2a shows a side sectional view of the fixing apparatus (2) set on the eye (1) together with the ultrasonic head (4b) of the ultrasonic biomicroscope, arranged in a suitable housing (4a). The ultrasonic head (4b) dips into the liquid located in the fixing apparatus (2) and is aligned with the main lobe of the emitted beam of sound in the direction of the set coagulation center (15) in the eye (1), thus making possible, e.g., a representation on the associated display, on which both the distal end of the fiber applicator (3) used and also the respective coagulation center (15) in the eye are visible in the B-image technique. The ultrasonic head (4b) of the ultrasonic biomicroscope is arranged for this purpose in the housing (4a) in such a manner that an oscillation or scanning in the plane of the drawing is possible, as shown by the corresponding arrow in FIG. 2a.

The actual section which corresponds to a possible visual representation on the display (12) in the B-image technique is indicated by the dotted line in FIG. 2a.

In order to make the fiber applicator used (3) sufficiently visible in the ultrasonic image of the B-image technique, and to guarantee an unambiguous differentiation from the surrounding tissue, it is advantageous to code at least the distal portion of the fiber applicator (3) in a suitable manner. For this purpose, this portion of the fiber applicator (3) is provided, e.g., with scattering bodies which cause a diffuse scattering of the ultrasonic waves and thus are clearly visible in the ultrasonic image. In the embodiment example shown, the fiber coating of the fiber applicator (3) is provided with small air bubbles as scattering bodies, as are shown schematically in FIG. 2a. Making the fiber applicator (3) visible by means of the corresponding coding is also found to be advantageous because, once the fiber applicator (3) has been localized in the ultrasonic image, a relatively simple localization of the set coagulation center is possible based on the known fiber radiation emission characteristic.

The coagulation center is then usually arranged a few mm beneath the surface of the eye.

The fixing apparatus (2) used in the first embodiment example shown in FIG. 2a essentially consists of two circular, telescoped cylinders (20a, 20b) with respective conical flanges formed on them. The two cylinders (20a, 20b) are rotatable relative to each other; the outer cylinder (20a) is seated firmly on the eye (1) to be treated, and the inner cylinder (20b) is arranged to be rotatable relative to this.

The fiber applicator used (3) is passed through a bore in the inner, rotatable cylinder (20b) so that the distal end of the fiber applicator (3) is seated on the sclera in the direction of the treatment site. The two cylinders (20a, 20b) are held together with a connecting element (21) in the form of a metal clamp.

The described first embodiment example of the fixing apparatus (2) accordingly makes possible a circular positioning of the fiber applicator (3) relative to the eye in discrete irradiation positions. The distal end of the fiber applicator and also the eye to be treated are thus arranged by means of this embodiment of the fixing apparatus in a defined and reproducible relationship to each other.

As an alternative to this, the fixing apparatus can also always be designed such that a spiral shape of positioning of the fiber applicator or of the set coagulation center is possible relative to the eye.

Figure 2B:
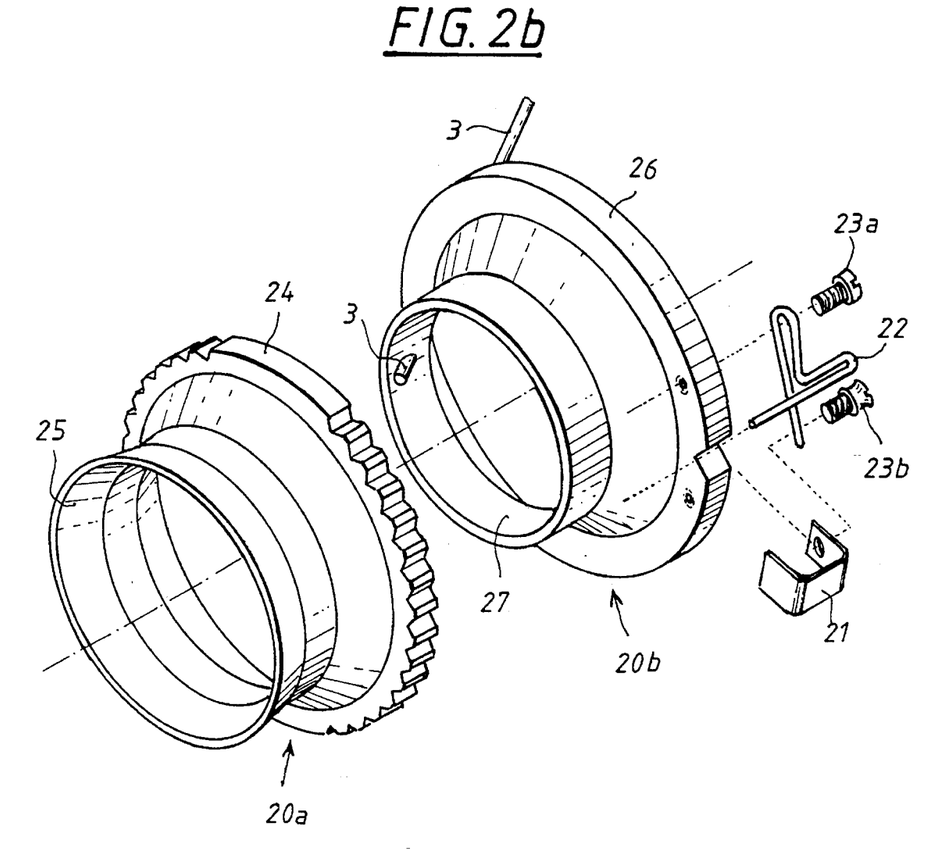

The fixing apparatus (2) of FIG. 2a is shown again in FIG. 2b in perspective, in dismantled form. The construction of the outer cylinder (20a), which consists of a cylindrical portion (25) which abuts the eye and an adjoining conical flange (24), is clearly evident here. The flange (24) has a structure like a gear wheel over certain regions of its periphery.

The inner cylinder (20b) likewise consists of an inner cylindrical portion (27), adjoined by a rotating flange (26) which widens out conically. This flange (26) then has the same outer diameter as the flange (24) of the outer cylinder (20a).

The two cylinders (20a, 20b) are held together in defined and reproducible relative positions by means of a fixing element (22) in the form of a suitably bent spring (22). The fixing element (22) is fastened for this purpose to the inner cylinder (20b) by means of a screw (23a), and engages by means of a V-shaped aperture in the flange (26) of this cylinder (20b) in the region, shaped like a gear wheel, of the flange (24) of the outer cylinder (20a). Thus every possible discrete relative position of the two cylinders (20a, 20b), i.e., thus also every possible relative position of the fiber applicator (3) relative to the eye, is reproducibly fixed.

Thus the radial distribution of the possible irradiation positions of the fiber applicator (3) can be set in a defined manner by a suitable choice of the size of the gearwheel-shaped regions of the flange (24) of the outer cylinder (20a). It is also possible here to make available different outer cylinders (20a) of this kind with different dimensions of this gearwheel-shaped region, specific to the patient.

The connecting element (21) in the form of a bent metal clamp is likewise shown in FIG. 2b; it is fastened to the inner cylinder (20b) by means of a screw (23b) and holds the two cylinders (20a and 20b) together.

Figure 2C:
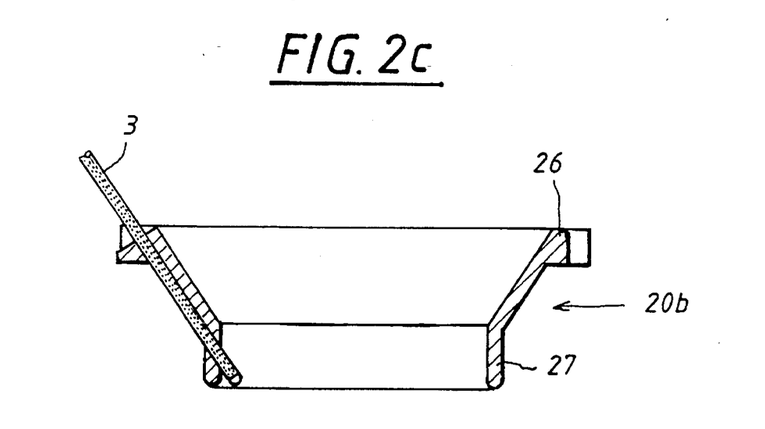
FIG. 2c shows a lateral sectional representation of a portion of the fixing apparatus of FIGS. 2a and 2b.

Finally, a side sectional view of the inner cylinder (20b) is shown in FIG. 2c. Clearly visible here, in particular, is how the fiber applicator (3) is arranged in bores of the flange (26) and of the cylindrical portion (27) of this cylinder (20b).

Figure 3:
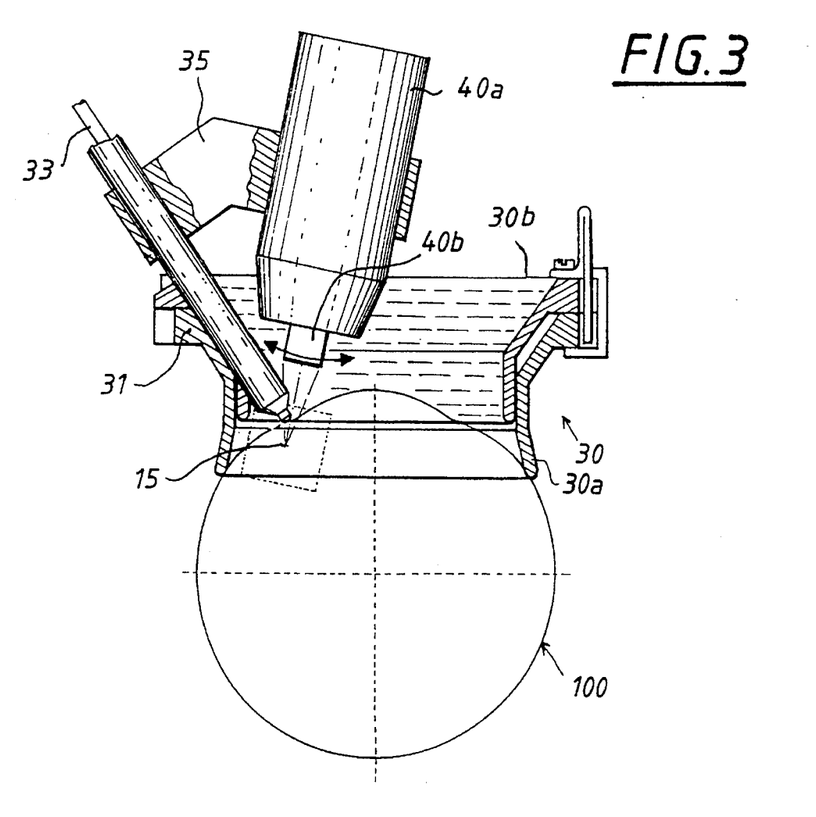
FIG. 3 shows a second embodiment example of a fixing apparatus in a side view.

A second possible embodiment of the fixing apparatus, arranged on the patient's eye, is shown in FIG. 3.

This embodiment example of the fixing apparatus (30) set on the patient's eye (100) likewise has in principle the same two-part construction of two rotatable cylinders (30a, 30b), one within the other, as the first described embodiment example. In contrast to the first described embodiment example from FIGS. 2a– 2c, however, no firm coupling is now provided between the fixing apparatus (30) and the distal end of the fiber applicator (33) used. It is now possible for the doctor to freely position the fiber applicator (33); however, the possibility exists of placing the distal end of the fiber applicator (33) on a support surface (31) of the fixing device (30), and a certain fixing and reproducibility of an irradiation position is ensured. The support surface (31) of the fixing apparatus (30) can here have, for example, suitable notches in which the fiber applicator (33) can be inserted, etc.

In addition, in this embodiment of the fixing apparatus (30) there is a mechanical coupling (35), which is preferably made rigid and adjustable, between the distal end of the fiber applicator (33) and the housing (40a) of the ultrasonic head (40b) of the ultrasonic biomicroscope. This coupling (35) is shown as a connecting strut between the fiber applicator (33) and the housing (40a), but this is only to indicate schematically the diverse possible varieties of coupling.

By means of this coupling (35) it is now ensured that the ultrasonic head (40b), after a pre-adjustment has been completed, always oscillates in a defined plane and hence makes possible in every case a sectional image representation of the region of interest in the eye (100), including the distal end of the fiber applicator (33). The fiber applicator (33) and the treatment site (15) then lie, in every possible irradiation position, in the plane of observation of the ultrasonic biomicroscope.

Thus the ultrasonic head (40b) does not have to be aligned anew with respect to the fiber applicator (33) on changing the irradiation position; on the contrary, because of the coupling (35) which is now provided, this alignment is ensured in every possible irradiation position once a pre-adjustment of the apparatus has been completed.

Sectional images are accordingly always generated by the ultrasonic biomicroscope from the ultrasonic head (40b) by means of this fixing apparatus, and on them the distal end of the fiber applicator (33) and thus also the site of coagulation (15) is visible to the doctor, e.g., in the B-image technique. The distal end of the fiber applicator (33) is again suitably coded, as in the previously described embodiment example, in order to ensure that it is discerned as well as possible in the ultrasonic image.

As already mentioned, the apparatus according to the invention enables the operating surgeon to choose between different operating modes of the ultrasonic biomicroscope and thus also between different representations on the display.

Possible visual representations on the display (12) in the B-image technique of the information supplied by the ultrasonic biomicroscope are described below with reference to FIGS. 4a and 4b.

Figure 4A:
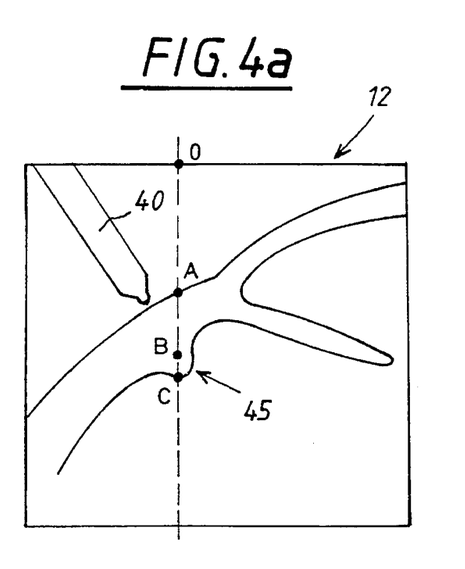
FIGS. 4a and 4b show the visual representation of the information supplied by the ultrasonic microscope on a display, before and after the setting of a coagulation in the B-image technique.

FIG. 4a shows a representation of the display (12) with regions of the front section of the eye including the distal end of the fiber applicator (40) used, before a coagulation. In order to make the fiber applicator (40) visible sufficiently well in the ultrasonic image, the distal portion of the fiber applicator (40) was coded, as described above; that is, the coating with suitable scattering bodies was provided.

The coagulation field in the eye, that is, the ciliary body (45) and its dimensions, is likewise perceptible to the doctor in the representation of the B-image technique.

A sectional line, passing through the field to be treated, i.e., the ciliary body (45), is furthermore shown in FIG. 4a; various relevant boundary surfaces in the eye are marked on it with the letters A, B and C. A one-dimensional depth image along this line can be generated by means of the utilization in the form of the A-image technique, as sketched below with reference to FIG. 5a–c. The position of the reflecting boundary surfaces can thereby be precisely determined at a known velocity of sound.

Figure 4B:
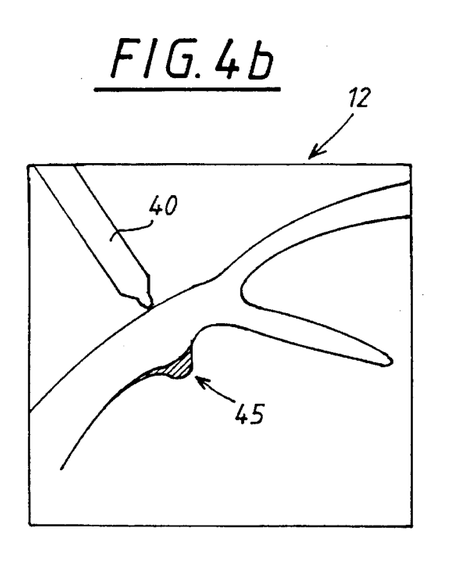

In FIG. 4b, the same field in the eye to be treated as in FIG. 4a can be seen after an at least partially completed laser treatment. The coagulation center set in the ciliary body (45) then effects the desired shrinkage of the ciliary body (45), which was made clearly visible to the doctor by a suitable false color representation of the shrunken field. By means of a suitable image processing software, those fields in the treated region of the eye are thus marked in which a tissue change took place as a result of the coagulation effects. The shrunken region is shown by shading in the representation of FIG. 4b.

The shrinking of the ciliary body (45) can thus be clearly followed by the doctor during the on-line observation of the laser treatment on the display (12). He varies the laser parameters at any given time, corresponding to the observed effects.

Further possibilities for the representation on the display (12) in the B-image technique of portions of the eye which are of interest are provided, for example, by a false color representation of the treated field in the eye in such a manner that the images of different stages of treatment are successively superimposed. For example, there can be superimposed on the image corresponding to the untreated state, one or more images which correspond to the state of the tissue after respective effected laser treatment. The resulting effects and changes due to the laser treatment in the region of the coagulation center are explicitly visible to the attending doctor in this differential representation.

From this representation of the treated section of the eye, it is furthermore possible for the attending doctor to plan the following therapeutic steps, i.e., thus if necessary to vary the laser power and/or the duration of irradiation. Besides this, there exist numerous further possibilities of representation, which can be realized according to the invention by means of suitable software, for the ultrasonic image in the B-image technique.

Possible graphical representations on the display (12) when the A-image technique is selected in the course of treatment will be described with reference to FIG. 5a–c. As already mentioned above, a one-dimensional depth image along the line drawn in on FIG. 4a is shown here.

The position of the depth image thereby generated can be suitably chosen by the doctor, by a corresponding alignment of the ultrasonic head.

In the graphical representation of the A-image technique, the length coordinate along the sectional line is shown in the direction of the abscissa; the reflected ultrasonic signal amplitudes are shown along the ordinate. The corresponding reflecting boundary surfaces from FIG. 4a are indicated by the letters A, B and C. The site of treatment, i.e., the ciliary body, is then located in region B; the boundary surfaces of this region along the one-dimensional depth image are marked in the representation of FIG. 5a–c with the notations $X_1$ and $X_2$.

Figure 5A:
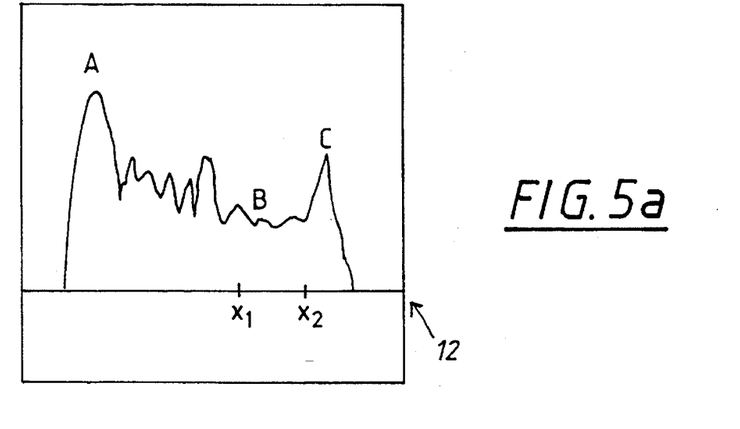
FIGS. 5a–5c respectively show the visual representation on a display of the information provided by the ultrasonic microscope in the A-image technique in the course of a treatment.
Figure 5B:
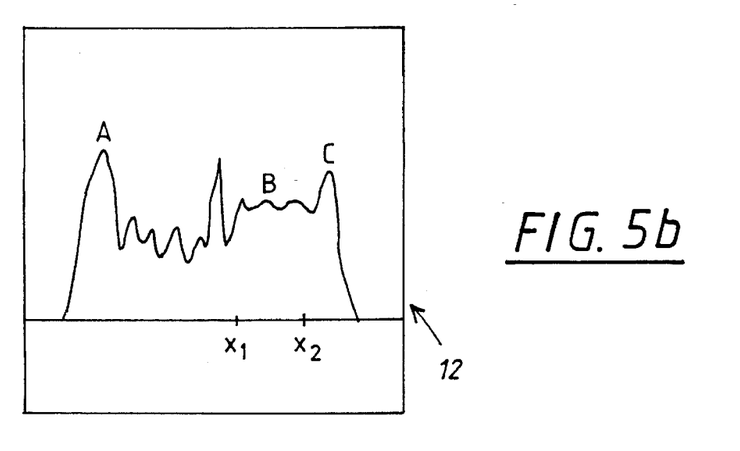
Figure 5C:
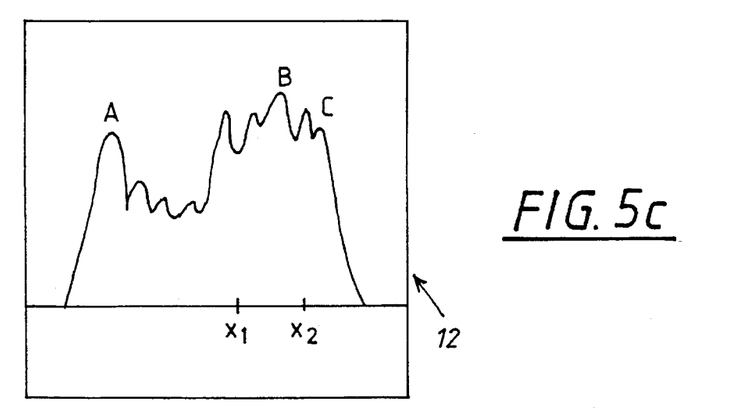

While FIG. 5a shows the source of the signal along the sectional line before the laser treatment, different stages of the subsequent laser treatment, and of the corresponding signal behavior, can be seen in FIGS. 5b and 5c. The desired shrinkage effect in the ciliary body region B can be clearly recognized; it brings about a significant change in the reflected ultrasonic signal in this region. The change of the signal amplitude in this region is to be attributed, inter alia, to the altered ultrasonic reflection properties of the shrunken ciliary body.

The doctor can accordingly follow the course of this signal explicitly on the display during the course of the laser cyclo-photocoagulation, and can end the laser treatment at this irradiation site at the desired signal amplitude, etc.

As already mentioned, the time course of the signal amplitude in this region can however also be used in an automated manner in a control or regulating circuit for the direct regulation of the laser used.

In a possible course of treatment, the operating surgeon selects one or more sectional lines of this kind from the first observed representation of the B-image technique; by means of a corresponding electronic gating of the region of interest, the resulting changes in this region can be precisely monitored, in the A-image technique, in the course of subsequent treatment. The signals from this region are used by means of the control or regulating circuit to vary the laser parameters correspondingly.

Figure 6:
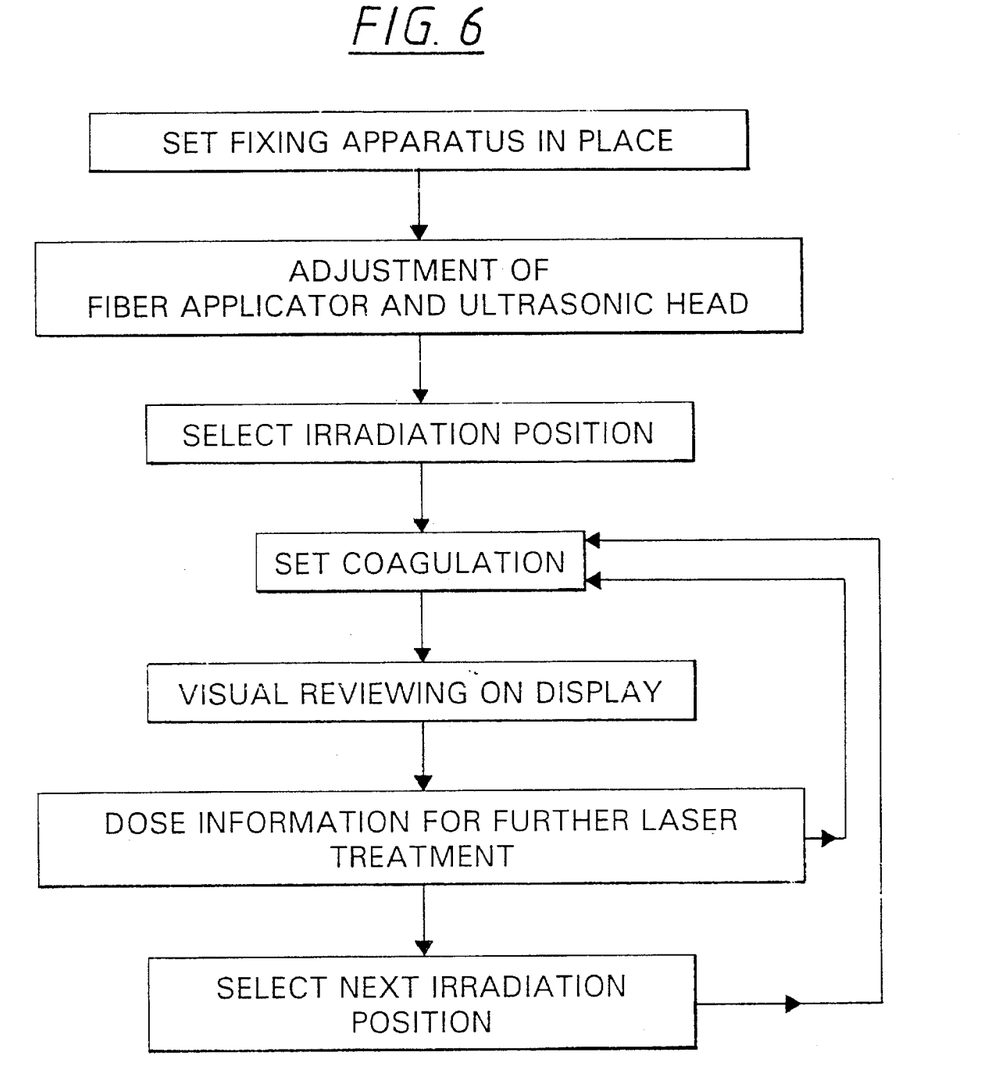
FIG. 6 shows a flow diagram of the possible course of treatment according to the method according to the invention.

A flow diagram of the possible course of the method according to the invention is shown in FIG. 6.

After the setting of the fixing apparatus on the patient's eye to be treated, the ultrasonic head of the ultrasonic biomicroscope is first aligned in a first adjustment step such that the fiber applicator (which is preferably coded) and the treatment site lie in the plane of observation of the ultrasonic biomicroscope, together with the coagulation center to be set. The first desired irradiation position can be selected at the same time as this adjustment.

When a fixing apparatus is used with the fiber applicator and ultrasonic head scan plane coupled together according to FIG. 3, the coupling has to be adjusted only once before the treatment, in such a manner that the distal end of the fiber applicator is visible in the image of the ultrasonic biomicroscope in every case.

The doctor then sets, by operation of the laser, a desired number of coagulations and visually reviews on the display, at intervals which he has selected, the obtained effects in the tissue. He accordingly obtains in each step of the process, from the supplied images of the ultrasonic biomicroscope, the required dose information for the further laser treatment. The choice between different operating modes of the ultrasonic biomicroscope, i.e. in particular between the A-image technique or the B-image technique, or else very varied representations on the display, is possible as previously described.

If the respectively set coagulation corresponds to the requirements, the position of the fiber applicator relative to the eye is then varied, i.e., a new irradiation position is thus chosen, and the process in the manner described is continued for the new coagulation center, and so on. It is here possible, according to the fixing apparatus used, to select the different irradiation positions by means of a fixing apparatus according to FIGS. 2a–2c, or else to freely select the irradiation positions when using a fixing apparatus according to the second described embodiment example of FIG. 3.

On the other hand, if the coagulation set for this irradiation position does not yet correspond to the requirements, a further application of laser irradiation, if necessary with altered power, etc., then takes place.

Since the doctor in addition follows the tissue changes in the course of the laser treatment, on line on the display, he can continuously draw from the observed shrinking of the ciliary body the necessary conclusions regarding the further course of the treatment.

We claim:

1. Apparatus for laser cyclo-photocoagulation comprising:
   fiber applicator means (3, 33, 40) for applying laser radiation for cyclo-photocoagulation, an ultrasonic head (4b, 40b) of an ultrasonic biomicroscope for monitoring said laser cyclo-photocoagulation,
   holding means for holding said fiber applicator means and said ultrasonic head in a defined relative orientation to each other, so that a treatment site for laser cyclo-photocoagulation and said fiber applicator means (3, 33, 40) lie in an observation plane of said ultrasonic biomicroscope in any possible irradiation position,
   and display means (12) connected with said ultrasonic biomicroscope for displaying a visual representation of said treatment site.

2. Apparatus according to claim 1, further comprising fixing and filling means (2, 30) for placement on an eye for fixing said eye in a defined position and for filling with a liquid.

3. Apparatus according to claim 1, further comprising image processing means (11) connected to said display means (12) for processing and representing images of investigated tissue, connected to follow said ultrasonic head (4b, 40b) of said ultrasonic biomicroscope, said image processing means including selection means for selecting between at least two operating modes of said ultrasonic biomicroscope.

4. Apparatus according to claim 3, wherein said two operating modes of said ultrasonic microscope comprise operating modes of A-image technique and B-image technique of said ultrasonic biomicroscope and include representations of said two operating modes on said display means (12).

5. Apparatus according to claim 4, in which said fiber applicator means (3, 33, 40) has a distal end and said ultrasonic head (4b, 40b) is oriented relative to said distal end of said fiber applicator means (3, 33, 40) such that said treatment site in said eye is visible on said display means (12) in said B-image technique mode of said ultrasonic biomicroscope.

6. Apparatus according to claim 5, in which said display means (12) provides in the B-image technique mode of said ultrasonic biomicroscope a differential representation of a section of said eye being worked on, with super-posed images of different treatment stages.

7. Apparatus according to claim 1, in which said fiber applicator means (3, 33, 40) is coded to provide an optimum discernment on said display means (12).

8. Apparatus according to claim 7, in which said fiber applicator means (3, 33, 40) is provided with a coating having integrated scattering elements that effect a diffuse scattering of ultrasonic waves emitted by said ultrasonic head (4b, 40b).

9. Apparatus according to claim 1, further comprising laser diode irradiation means (6) providing an irradiation source for said fiber applicator means (3, 33, 40).

10. Apparatus according to claim 1, further comprising laser radiation means for providing laser radiation having laser wavelengths that lie in a region of 0.5 μm–1.7 μm.

11. Apparatus according to claim 2, in which said fiber applicator means (3, 33, 40) has a distal end that is positioned by said fixing means (2, 30) circularly relative to said eye (1, 100).

12. Apparatus according to claim 11, wherein said fixing means (2, 30) comprises an outer cylinder (20a) and an inner cylinder (20b) that is rotatable relative to said outer cylinder, said outer cylinder (20a) assumes a fixed relative position to said eye (1, 100), said inner cylinder (20b) is rotatable relative to said fixed relative position, and said distal end of said fiber applicator means (3, 33, 40) is firmly connected to said inner cylinder (20b).

13. Apparatus according to claim 1, in which said fiber applicator means (3, 33, 40) has a distal end, further comprising a mechanical coupling (35) connected to said fiber applicator means and said ultrasonic head for establishing said defined relative orientation between said distal end of said fiber applicator means (3, 33, 40) and said ultrasonic head (40b) of said ultrasonic biomicroscope.

14. Method for laser cyclophotocoagulation, comprising the steps of:

monitoring a course of treatment in an eye (1, 100) on a display (12) of an ultrasonic biomicroscope, an ultrasonic head of said ultrasonic biomicroscope being aligned towards a treatment site, and utilizing information acquired by means of said ultrasonic biomicroscope for regulation of applied laser irradiation during said course of treatment.

15. Method according to claim 14, in which said acquired information is directly utilized by means of a control circuit or regulating circuit for regulation of said applied laser radiation.

16. Method according to claim 14, further comprising adjusting a fiber applicator (3, 33, 40) relative to said ultrasonic head (4b, 40b) so that a distal end of said fiber applicator (3, 33, 40) and a treatment site are simultaneously visible in an ultrasonic image in a B-image technique mode, laying down at least one sectional line through a region to be treated in said eye (1, 100), along which line a one-dimensional representation is possible in an A-image technique mode, and utilizing behavior with time, in said course of treatment, of signal amplitude in a representation of said A-image technique mode in said region of treatment for regulation of applied laser power.

* * * * *